United States Patent [19]
Ishizaki et al.

[11] Patent Number: 5,475,062
[45] Date of Patent: Dec. 12, 1995

[54] METHOD FOR SURFACE TREATMENT OF ABSORBENT RESIN

[75] Inventors: Kunihiko Ishizaki, Suita; Shin-ichi Fujino; Kinya Nagasuna, both of Himeji; Yoshiniko Masuda, Takarazuka, all of Japan

[73] Assignee: Nippon Shokubai Co., Ltd., Osaka, Japan

[21] Appl. No.: 186,560

[22] Filed: Jan. 26, 1994

[30] Foreign Application Priority Data

Jan. 26, 1993 [JP] Japan .................. 5-10905

[51] Int. Cl.$^6$ .................. C08F 8/14
[52] U.S. Cl. .................. 525/384; 525/329.5; 525/329.7
[58] Field of Search .................. 524/389, 387, 524/388; 525/329.5, 329.7, 384

[56] References Cited

U.S. PATENT DOCUMENTS 5,229,466  7/1993  Brehm et al. .................. 525/329.9

FOREIGN PATENT DOCUMENTS

| 450924 | 10/1991 | European Pat. Off. . |
|---|---|---|
| 0450924A2 | 10/1991 | European Pat. Off. . |
| 0509708A1 | 10/1992 | European Pat. Off. . |
| 0514724A1 | 11/1992 | European Pat. Off. . |
| 59-80459 | 5/1984 | Japan . |
| 3-195705 | 8/1991 | Japan . |
| 2127832A | 4/1984 | United Kingdom . |

*Primary Examiner*—Jeffrey T. Smith
*Attorney, Agent, or Firm*—Burns, Doane, Swecker & Mathis

[57] ABSTRACT

A method for the surface treatment of an absorbent resin is proposed which notably improves the absorption capacity of the absorbent resin under pressure without impairing safety and hydroscopic flowability. The method comprises adding an organic carboxylic ester of a polyhydric alcohol to the absorbent resin and then heat-treating the resultant mixture.

14 Claims, 1 Drawing Sheet

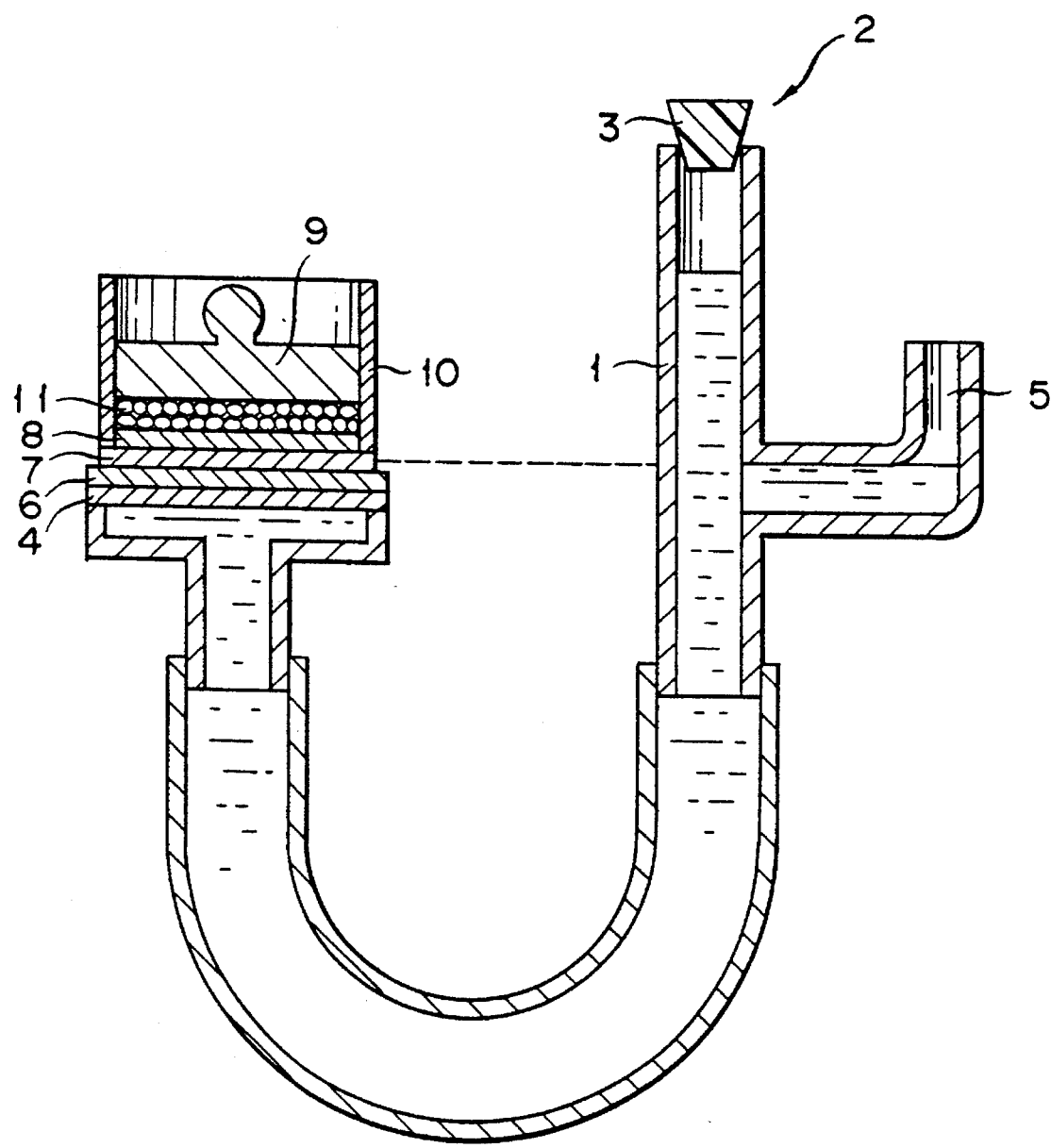
FIGURE

METHOD FOR SURFACE TREATMENT OF ABSORBENT RESIN

BACKGROUND OF THE INVENTION

1. Field of the Invention

This invention relates to a method for the surface treatment of an absorbent resin. More particularly, it relates to a method for the surface treatment of an absorbent resin, which method is ideal for the production of an absorbent agent exhibiting excellent physical properties such as a high capacity for absorption under load, excels in safety, and hydroscopic flowability.

2. Description of the Prior Art

In recent years, absorbent resins which absorb a large volume of water and consequently take on the form of gel have been developed and have been finding extensive utility in the field of agriculture and forestry and the field of civil engineering as well as in the field of sanitary materials such as disposable diapers and sanitary napkins.

The absorbent resins heretofore known in the art include cross-linked polyacrylic salts, hydrolyzed starch-acrylonitrile graft polymer, starch-acrylic acid (acrylic salt) graft polymer, saponified cross-linked vinyl acetate-acrylate copolymers, cross-linked polyacrylamide, cross-linked polymer of 2-acrylamide-2-methyl propanesulfonic acid (propanesulfonic salt), hydrolyzed cross-linked polyacrylamide, and cross-linked cationic monomers, for example.

These absorbent resins are insolubilized hydrophilic resins which have a uniform cross-linked structure in their polymeric units. Generally, the particles of these absorbent resins have their surfaces additionally cross-linked as with a cross-linking agent to impart a cross-link density gradient to the particles and enable the absorbent resins to acquire improved physical properties as evinced by addition to the absorption rate of water, preclusion of the formation of wet clusters of particulate resin, exaltation of gel strength, improvement in the absorption capacity of water under load, prevention of the phenomenon of gel blocking, and enhancement of the liquid permeability. In the case of the absorbent resins which have such functional groups as, for example, a carboxyl group or a hydroxyl group, since the surface treatment mentioned above affects the basic physical properties of the absorbent resins to a large extent, numerous cross-linking agents and many methods for their mixing have been proposed to date.

The methods heretofore proposed for the mixing of cross-linking agents are broadly divided into those comprising dispersing an absorbent resin in a solvent (JP-A-56-131,608, JP-A-57-44,627, JP-A-58-42,602, and JP-A-58-117,222) and those comprising directly adding a treating agent or a solution of the treating agent to an absorbent resin. In the case of the latter methods which comprise direct addition of a cross-linking agent, many methods have been proposed for ensuring uniform addition of a cross-linking agent and water. These methods include a method which relies on the use of an inert inorganic powder (JP-A-60-163,956 and JP-A-60-255,814), a method which comprises first adding a cross-linking agent and subsequently exposing it to steam (JP-A-1-113,406), a method which resides in heating a cross-linking agent under specific humidity conditions (JP-A-1-297,430), a method which resorts to the use of a mixed solvent comprising water and a polyhydric alcohol (JP-A-63-270,741, JP-A-64-56,707, and JP-A-1-292,004), and a method which involves the use of a mixed solvent consisting of water and an ether compound (JP-A-2-153,903), for example.

As typical examples of the cross-linking agents proposed to date, polyglycidyl compounds, haloepoxy compounds, polyisocyanate compounds, polyaziridine compounds (JP-A-59-189,103), polyoxazoline compounds, polyamine compounds, polyhydric alcohols (JP-A-58-180,233 and JP-A-61-16,903), alkylene carbonates (DE-A-4020780C), glyoxals (JP-A-52-117,393), polyvalent metal salts (U.S. Pat. No. 4,043,952, JP-A-61-257,235, JP-A-62-7,745), silane coupling agents (JP-A-61-211,305, JP-A-61-252,212, and JP-A-61-264,006), peroxide radical initiators (JP-A-63-99,211), and special glycidyl compounds of specific structures (JP-A-62-50,305, JP-A-61-213,206, JP-A-63-199,205, JP-A-63-118,308, JP-A-487,638, JP-A-1-201,312, and JP-A-61-293,228) may be cited.

These cross-linking agents are broadly divided into (1) ring-opening reactive cross-linking agents such as glycidyl compounds, (2) condensation reactive cross-linking agents such as isocyanate compounds, (3) ion-bonding crosslinking agents such as polyvalent metals, and (4) dehydration reactive cross-linking agents such as polyhydric alcohols.

In the four kinds of cross-linking agents mentioned above, the ion-bonding cross-linking agents of the kind of (3) do not withstand actual use because they are deficient in the binding force with an absorbent resin. The cross-linking agents of the kinds of (1) to (3), because of their high reactivity, react immediately with an absorbent resin on contact therewith and alter the physical properties of the absorbent resin and, therefore, encounter difficulty in being uniformly distributed in the surface region of the absorbent resin over a long duration following the time of mixture. In spite of the numerous methods proposed for the addition of a cross-linking agent as described above, it is difficult to attain uniform cross-linkage of an absorbent resin with the cross-linking agents of the kinds of (1) to (3) and permit impartation of ideal physical properties to the absorbent resin. Generally, when a cross-linking agent is used in cross-linking an absorbent resin, part of the cross-linking agent remains in an unaltered form in the absorbent resin without reference to the kind of the crosslinking agent. The fact that such a cross-linking agent as a glycidyl compound which has high reactivity remains, if partly, in the unaltered form on the surface of an absorbent resin is undesirable from the standpoint of safety. A method for decreasing the amount of the remaining cross-linking agent, therefore, has been proposed (JP-A-3-195,705). This method is at a disadvantage in entailing a complicated process and, moreover, attaining the expected decrease only with great difficulty.

Unlike the cross-linking agents of the kinds of (1) to (3), such dehydration reactive cross-linking agents of the kind of (4) as polyhydric alcohols are free from the disadvantage of reacting with an absorbent resin immediately after their contact with the absorbent resin. They are, therefore, distributed gradually and uniformly on the surface of the absorbent resin and allowed to effect a uniform surface treatment easily on the absorbent resin. Polyhydric alcohols generally have high stability and safety and, therefore, pose no problem if they happen to persist on the surface of an absorbent resin. Thus, polyhydric alcohols have been used particularly preferably as a cross-linking agent in the surface treatment of an absorbent resin from the standpoint of physical properties and safety.

Since cross-linking agents such as of polyhydric alcohols generally exhibit extremely high degrees of hydrophilicity and hygroscopicity, they possibly permeate an absorbent resin to a great depth at a sacrifice of the effect of surface treatment, depending on the conditions of mixture and the reaction conditions. When these cross-linking agents of polyhydric alcohols remain on the surface of the absorbent resin, they exalt the hygroscopicity and adhesiveness of the treated absorbent resin after absorbing moisture excessively. When the absorbent resin resulting from this surface treatment is put to actual use in a factory full of moisture as in a rainy season, therefore, it entails the disadvantage that the particulate mass of the absorbent resin agglomerate and induce the phenomenon of blocking.

For the purpose of preventing the absorbent resin from this mischief of blocking, a method which resorts to addition of a fine inorganic powder having an approximate particle diameter of several microns to the absorbent resin has been proposed (JP-A-59-80,459). This method, however, has the disadvantage that the fine inorganic powder is extremely expensive and, on being drifted as in wind, is liable to imperil the worker's health and impair the plant's operational efficiency.

An object of this invention, therefore, is to provide a method for the surface treatment of an absorbent resin.

Another object of this invention is to utilize the surface treatment for producing an absorbent resin which (1) excels in safety, (2) manifests an effect in ensuring uniform mixture with a cross-linking agent and consequently improving the physical properties of the absorbent resin, and (3) avoids inducing agglomeration of the particulate mass of the absorbent resin even in a highly humid atmosphere.

SUMMARY OF THE INVENTION

The objects described above are accomplished by a method for the surface treatment of an absorbent resin which comprises adding an organic carboxylic ester of a polyhydric alcohol to the absorbent resin and then heat-treating the resultant mixture.

The method of this invention for the surface treatment of an absorbent resin by the use of an organic carboxylic ester of a polyhydric alcohol has such features as are indicated in (1) through (3) below.

(1) The surface treatment of this invention brings about an excellent effect because the organic carboxylic ester is easily incorporated uniformly in the absorbent resin, easily distributed gradually and uniformly on the surface of the absorbent resin particles, and sparingly allowed to permeate the absorbent resin to a large depth.

(2) Unlike the cross-linking agent such as of polyglycidyl compound, the organic carboxylic ester remaining on the surface of the absorbent resin is safe.

(3) The absorbent resin resulting from the surface treatment does not easily entail the phenomenon of blocking and excels in hydroscopic flowability even in a highly humid atmosphere.

BRIEF DESCRIPTION OF THE DRAWING

FIGURE is a cross section of an absorption capacity measuring apparatus used under load in this invention.

EXPLANATION OF THE PREFERRED EMBODIMENT

Now, this invention will be described more specifically below.

The absorbent resin which is subjected to the surface treatment in this invention is an absorbent resin which, in water, absorbs a large volume of the water and consequently swells and takes up the form of hydrogel. The absorbent resins which answer this description include cross-linked polyacrylic salts, hydrolyzed starch-acrylonitrile graft polymer, starch-acrylic acid (acrylic salt) graft polymer, saponified cross-linked vinyl acetate-acrylic ester copolymers, cross-linked 2-acrylamide-2-methylpropanesulfonic acid (salt) polymer, hydrolyzed cross-linked polyacrylamide, and neutralized cross-linked isobutylene-maleic anhydride copolymer, for example. Among other absorbent resins mentioned above, those which contain a carboxyl group or a hydroxyl group prove particularly desirable.

These absorbent resins are generally obtained by polymerizing such hydrophilic unsaturated monomers as acrylic acid (salt), methacrylic acid (salt), 2-(meth)acryloyl ethanesulfonic acid (salt), 2-(meth)acrylamide-2-methyl propanesulfonic acid (salt), methoxy polyethylene glycol (meth)acrylate, N,N-dimethylaminoethyl (meth)acrylate, acrylamide, and vinyl acetate. During this polymerization, such a hydrophobic unsaturated monomer as butadiene, isobutene, ethylene, propylene, or stearyl (meth)acrylate may be additionally used in a small amount. It is particularly preferable to use, among other hydrophobic unsaturated monomers mentioned above, acrylic acid (salt) in an amount of not less than 50 mol %.

The acid group such as, for example, a carboxyl group in the absorbent resin is preferable to have been neutralized in a ratio in the range of 30 to 100 mol %, preferably 40 to 95 mol %, and more preferably 50 to 80 mol %. The basic substances which are effectively usable for the neutralization include (hydrogen) carbonates, hydroxides of alkali metals, ammonia, and organic amines, for example.

The method of cross-linking to be adopted for the formation of the absorbent resin is not particularly restricted. The polymerization for the production of the absorbent resin, however, is preferable to be carried out in the presence of a prescribed amount of an internal cross-linking agent. The internal cross-linking agents which are effectively usable for the polymerization include N,N'-methylenebis-acrylamide, (poly)ethylene glycol di(meth)acrylate, (poly)propylene glycol di(meth)acrylate, trimethylolpropane tri(meth)acrylate, trimethylolpropane di(meth)acrylate, (poly)ethylene glycol di(β-acryl oxypropionate), poly(meth)allyloxy alkane, glycerol acrylate methacrylate, (poly)ethylene glycol diglycidyl ether, ethylene glycol, polyethylene glycol, glycerol, pentaerythritol, ethylenediamine, and polyethyleneimine, for example. These internal cross-linking agents may be used either singly or in the form of a mixture of two or more members. The amount of such an internal cross-linking agent to be used is preferable to be in the range of preferably 0.005 to 5 mol %, more preferably 0.01 to 1 mol %, based on the amount of the monomer.

In this invention, though the polymerization of the monomer may be carried out in the manner of either bulk polymerization or precipitation polymerization, the monomer is generally preferable to be used in the form of a solution in water or an aqueous liquid. Though the concentration of the monomer in the solution is not particularly inhibited from surpassing the level of saturation, it is generally preferable to be in the range of 20% by weight to the saturated concentration. The monomer system prepared for the polymerization may incorporate therein such a hydrophilic polymeric compound as starch, cellulose or a derivative thereof, polyacrylic acid, polyvinyl alcohol, or a cross-linked polyacrylic salt and such a water-soluble chain transfer agent as hypophosphorous acid (salt), for example.

The method to be used for the polymerization of the monomer mentioned above is not particularly limited. The polymerization, however, is preferable to be effected by the use of a radical polymerization initiator. The method to be adopted for this radical polymerization may be any of the known methods such as, for example, aqueous solution polymerization, reversed-phase suspension polymerization, reversed-phase emulsion polymerization, precipitation polymerization, and bulk polymerization. Among other methods cited above, aqueous solution polymerization or reversed-phase suspension polymerization prove particularly preferable.

The radical polymerization initiator to be used herein may be any of the known polymerization initiators such as, for example, sodium persulfate, t-butyl hydroperoxide, hydrogen peroxide, and 2,2'-azo-bis(2-amidinopropane) dihydrochloride. The combined use of this initiator with such a reducing agent as (hydrogen) sulfurous acid (salt) or L-ascorbic acid or with ultraviolet light is not particularly inhibited. The amount of this initiator or reducing agent to be used is generally in the range of 0.001 to 2 mol %, preferably 0.01 to 0.5 mol %.

Although the gel polymer resulting from the polymerization may be subjected to the surface treatment as an absorbent resin of the present invention as it is, the gel polymer resulting from the polymerization may be optionally dried, depending on the purpose for which it is used or the solids content of the polymer. The method to be used for this drying does not need to be particularly limited but may be selected from among various known methods. The gel polymer is desired to be dried until the solids content thereof reaches a level above 60% by weight, preferably 90% by weight.

After the polymerization or after the drying, the absorbent resin may be further pulverized or pelletized for the purpose of adjusting the particle size thereof. Where the absorbent resin is desired to be in a powdery form to suit the purpose of use, it is adjusted to an average particle diameter in the approximate range of 10 to 2,000 μm, preferably 100 to 1,000 μm, and more preferably 300 to 600 μm. After this adjustment, the absorbent resin is preferable to have the narrowest possible particle size distribution.

The surface treatment contemplated by this invention is accomplished by first adding an organic carboxylic ester of a polyhydric alcohol (hereinafter referred to simply as "polyhydric alcohol ester") to the absorbent resin and heat-treating the resultant mixture without fail.

Though the polyhydric alcohol ester which is essentially used in this invention does not need to be particularly limited, it is preferable to be an ester which is not possessed of a plurality of unesterified hydroxyl groups. Specifically, the number of hydroxyl groups in the molecular unit thereof is 0 or 1, preferably 0. This polyhydric alcohol ester may be possessed of a functional group in the form of free carboxyl group, phosphoric acid group, sulfonic acid group, or an (in)organic salt thereof.

The polyhydric alcohol ester is generally obtained on the basis of a polyhydric alcohol or a cyclic ether which is the precursor of the polyhydric alcohol. As typical examples of the polyhydric alcohol ester, esterified diols (such as, for example, esters of ethylene glycol, diethylene glycol, triethylene glycol, tetraethylene glycol, polyethylene glycol, 1,2-propylene glycol, 1,3-propylene glycol, 2,2-dimethyl-1,3-propanediol, 2,2,4-trimethyl-1,3-pentanediol, 1,3-butanediol, 1,4-butanediol, 2-butene-1,4-diol, 2-butyne-1,4-diol, 1,5-pentanediol, 1,6-hexanediol, 1,2-cyclohexane diol, 1,3-cyclohexane dimethanol, 1,2-cyclohexanediol, 1,3-cyclohexanediol, 1,4-cyclohexanediol, 1,7-heptanediol, 1,8-octanediol, 2-ethyl-1,3-hexanediol, 1,9-nonanediol, 1,10-decanediol, 1,12-dodecanediol, N-methyl diethanol amine, N-ethyl diethanol-amine, N-butyl diethanol amine, and glycerophosphoric acid), esterified triols (such as, for example, esters of glycerol, 2-ethyl-2-hydroxymethyl-1,3-propanediol, and trimethylol propane), esterified tetrols (such as, for example, esters of pentaerythritol), esterified hexanols (such as, for example, esters of dipentaerythritol and sorbitol), esterified octanols (such as, for example, esters of tripentaerythritol), and esters of polyglycerol may be cited. Among other polyhydric alcohol esters cited above, the polyhydric alcohol esters derived from ethylene glycol, diethylene glycol, triethylene glycol, polyethylene glycol, diethanolamine, triethanolamine, glycerol, trimethylolpropane, 1,3-propanediol, 2,3-propanediol, pentaerythritol, sorbitol, polyglycerol, and glycerophosphoric acid prove particularly desirable.

The polyhydric alcohol esters mentioned above are obtained on the basis of organic carboxylic acids or derivatives thereof. As typical examples of the polyhydric alcohol ester so obtained, esters of such monocarboxylic acids as formic acid, acetic acid, propionic acid, butanoic acid, isobutanoic acid, pentanoic acid, isopentanoic acid, neopentanoic acid, hexanoic acid, heptanoic acid, glyceric acid, 3-phosphoglyceric acid, and lactic acid, half esters of such dicarboxylic acids as succinic acid, malonic acid, fumaric acid, tartaric acid, and malic acid, monoester of tricarboxylic acids such as citric acid, and aromatic carboxylic esters such as benzoic acid may be cited. The half ester of a dicarboxylic acid mentioned above refers to the product of such esterification of the dicarboxylic acid that one of the two carboxylic acids thereof has been exclusively esterified and the other carboxylic acid has remained in its unaltered form. The organic carboxylic acids mentioned above may be possessed of an unsaturated double bond or a halogen atom in the molecular unit thereof.

In the polyhydric alcohol esters mentioned above, the esters of lower carboxylic acids prove preferable, the esters of such lower carboxylic acids as are possessed of not more than 7 carbon atoms prove more preferable, and one or more members selected from the group consisting of formic esters, acetic esters, propionic esters, acrylic esters, butanoic esters, lactic esters, succinic half esters, fumaric half esters, tartaric half esters, and malic half esters prove still more desirable from the standpoint of the effect of surface treatment and the properness of reactivity. Most preferably, acetic esters are used in the present invention.

As typical examples of the polyhydric alcohol ester which is effectively used in this invention, diesters (such as diformates, diacetates, and dipropionates) of diols (ethylene glycol, diethylene glycol, triethylene glycol, polyethylene glycol, diethanolamine, 1,3-propanediol, and 2,3-propanediol); triesters or diesters (such as triformates, triacetates, tripropionates, and diacetates) of triols i(triethanol amine, glycerol, and trimethylol propane); pentaesters or tetraesters (such as pentaformates, pentaacetates, pentatripropionates, and tetraacetates) of pentaerythritol; hexaesters or pentaesters (such as hexaformates, hexaacetates, hexatripropionates, and pentaacetates) of sorbitol; and polyesters of polyglycerol may be cited. Further, in addition, esters of polyvalent alcohols having a plurality of hydroxyl groups such as monoester of the above-mentioned triols, e.g., glycerol monoacetate may be cited.

The amount of the polyhydric alcohol ester to be used in this invention is generally in the range of 0.01 to 20 parts by weight, preferably 0.2 to 10 parts by weight, based on 100 parts by weight of the solids content of the absorbent resin.

The addition of the polyhydric alcohol ester to the absorbent resin is effected by any of the known methods such as, for example, a method which comprises directly adding the polyhydric alcohol ester, a solution of the relevant polyhydric alcohol ester in an organic solvent, or a solution of the polyhydric alcohol ester in a mixed solvent comprising the organic solvent and water to the absorbent resin or a method which comprises adding the polyhydric alcohol ester to the absorbent resin dispersed in advance in a solvent. When the former method is adopted, an organic compound such as finely divided silicon oxide or a surfactant may be used for the purpose of ensuring more uniform addition of the polyhydric alcohol ester.

The polyhydric alcohol ester may be added directly optionally in the form of a polyhydric alcohol ester solution or a dispersion to the absorbent resin. The solvents which are desirably usable for the preparation of the solution or the dispersion may include such hydrophilic solvents as methyl alcohol, ethyl alcohol, n-propyl alcohol, isopropyl alcohol, acetone, and tetrahydrofuran, for example. The amount of the solvent to be used is in the range of 0 to 20 parts by weight, preferably 0 to 8 parts by weight, based on 100 parts by weight of the solids of the absorbent resin.

In this invention, after the absorbent resin has been mixed with the polyhydric alcohol ester, the heat treatment to be given to the resultant mixture is preferable to proceed in the presence of water from the standpoint of the effect of the heat treatment. When the absorbent resin to be used in this case happens to be in a dry state, therefore, the water is preferable to be added to the absorbent resin either together with or separately from the polyhydric alcohol ester. The amount of the water thus added is preferable not to exceed 20 parts by weight, preferably to fall in the range of 0.5 to 10 parts by weight, based on 100 parts by weight of the solids content of the absorbent resin.

The polyhydric alcohol ester is inert to the absorbent resin at room temperature and therefore does not entail the disadvantage of reacting with the absorbent resin at once on contact therewith. Thus, it enjoys the advantage that it is mixed uniformly and easily with the absorbent resin. And it can be easily carried out even on the absorbent resin having a high water content or on the hydrogel fresh from the polymerization presumably because the polyhydric alcohol ester is hydrophobic and permeates the absorbent resin to a large depth only with difficulty, so the heat treatment and drying can be easily made to proceed at the same time.

After the absorbent resin has been mixed with the polyhydric alcohol ester in accordance with the procedure described above, this invention requires the resultant mixture to be given the heat treatment without fail. When this heat treatment is not given to the mixture, the effective improvement of physical properties aimed at by this invention is not obtained. At times, the omission of the heat treatment may possibly result in degradation of physical properties.

The temperature of the heat treatment is in the range of 100° to 300° C., preferably 150° to 250° C., and more preferably 170° to 240° C. If this temperature is lower than 100° C., the heat treatment consumes a long time to impair productivity and render it difficult to carry out the heat treatment uniformly and stably. Conversely, if the temperature exceeds 300° C., the possibility ensues that the absorbent resin will be thermally degraded. Though the duration of the heat treatment is properly selected to suit the expected effect of the heat treatment and the temperature of the heat treatment, it is generally in the range of 1 minute to 10 hours, preferably 10 minutes to 2 hours.

The heat treatment can be carried out by any of the known methods such as, for example (1) a method which comprises directly adding the polyhydric alcohol ester or a solution thereof (dispersant thereof) to the absorbent resin and subsequently heat-treating the mixture in its unaltered form, (2) a method which comprises adding the polyhydric alcohol ester to the absorbent resin dispersed in advance in a solvent and subsequently heat-treating the dispersion in its unaltered form, and (3) a method which comprises separating the mixture by filtration from the dispersion and heat-treating the separated mixture. In these conventional methods, the method of (1) or (2) which avoids using a large amount of solvent desirable. The method of (1) proves particularly desirable. The device to be used for the heat treatment is not particularly limited. The heat treatment is carried out by the use of any of the known devices such as, for example, a hot air drier, a fluidized-bed drier, and a Nauter type drier.

The method of heat treatment according with this invention manifests an excellent effect in performing the heat treatment. Even when the polyhydric alcohol ester happens to remain partly on the surface of the absorbent resin, it poses no problem about safety. Moreover, the produced absorbent resin exhibits a notably improved ability to resist the trouble of blocking in a highly humid atmosphere. Thus, it can be stably used even in a factory which is full of highly humid air.

The absorbent resin of this invention has high absorption capacity under load of not less than 25 g/g and is an absorbent particulate resin having the surface region thereof cross-linked enough to avoid the mischief of blocking for at least 30 minutes at 25° C. at a relative humidity of 50%. It is a novel absorbent resin powder which neither contains any expensive finely divided inorganic substance prone to invade the worker's respiratory system or deteriorate the workability nor induces the phenomenon of blocking in a highly humid atmosphere. Since the absorbent resin of this invention incorporates no finely divided inorganic substance therein, it is substantially composed of particles measuring not less than 1 μm. These particles have an average diameter in the range of 100 to 1,000 μm, preferably 300 to 600 μm. They are in an irregular shape or a spherical shape. They are desired to be in the irregular shape which is susceptible less to exfoliation as from the core in a diaper, for example.

Now, this invention will be described more specifically below with reference to working examples. It should be noted, however, that the scope of this invention is not limited to these working examples. The physical properties of the absorbent resin to be described in the working examples represent data which have been determined by the methods shown below.

The properties of the absorbent resin have been determined by the following methods.

(a) Absorption capacity (without load)

This property was determined by uniformly placing 0.2 g of a given absorbent resin in a teabag-like pouch (40×150 mm) of nonwoven fabric, immersing the pouch containing the sample in an aqueous 0.9 wt % sodium chloride solution (physiological saline solution), removing the wet pouch from the solution after 30 minutes' standing therein, allowing the solution to strain out of the wet pouch for a prescribed length of time, weighing the pouch to find the weight (W1), repeating the same procedure while avoiding use of the absorbent resin, finding the weight (W0) of the wet pouch, and performing the calculation of the following formula 1.

Absorption capacity $(g/g)$=(Weight $I_1$ after absorption $(g)$– Weight $W_o$ of blank $(g)$)/(Weight of absorbent resin $(g)$)     (1)

(b) Absorption capacity under load

With the aid of an apparatus constructed as illustrated in Figure, this property was determined by plugging an upper mouth 2 of a buret 1 with a stopper 3, setting a measuring base 4 and an air inlet 5 at an equal level, placing a filter paper 7 on a glass filter 6 of a diameter of 70 mm located in the central part of the measuring base 4, fixing a non-woven fabric 8 at the lower terminal part of a supporting cylinder 10 of a diameter of 55 mm, uniformly scatting 0.2 g of a given absorbent resin 11 on the non-woven fabric 8, placing a load of 20 g/cm² on the scattered sample 11, mounting the total of non-woven fabric, absorbent resin, and load as held in the supporting cylinder on the filter paper 7 spread on the glass fiber 6, allowing artificial urine (containing 1.9% of urea, 0.8% of NaCl, 0.1% of $CaCl_2$, and 0.1% of $MgSO_4$) to be absorbed by the absorbent resin for 30 minutes thereby finding the volume (A ml) of the artificial urine so absorbed, and performing the calculation of the following formula 2.

Absorption capacity under load $(ml/g)$= $A(ml)/0.2(g)$     (2)

(c) Suction power

This magnitude was determined by pouring 20 ml of artificial urine over tissue paper thereby preparing a substrate material containing the artificial urine, placing 1 g of a given absorbent resin on the tissue paper and, after the elapse of 10 minutes, collecting a swollen gel, and weigh the gel thereby finding suction powder (g/g).

(d) Hygroscopic flowability

This property was determined by uniformly scattering 2 g of a given absorbent resin of JIS 20-mesh pass in an aluminum cup 52 mm in diameter, allowing the scattered absorbent resin in the aluminum cup to stand in a constant temperature and humidity bath kept at 25° C. and 50% of humidity for 30 minutes, then mounting the aluminum cup now containing the absorbent resin in a humid state on a micro type electromagnetic shaker (produced by Tsutsui Rikagaku K.K. and marketed under product code of "M-2"), vibrating the shaker at a scale reading of 8 for 10 seconds, and visually examining the absorbent resin particles on the aluminum cup as to flowability.

The results were rated on the four-point scale, wherein ⊙ stands for good flowability, ○ for partial adhesion of resin particles to the aluminum cup, △ for rather heavy adhesion of resin particles to the aluminum cup, and X for complete agglomeration of resin particles in a blocked state, indicating absence of flowability.

Production Example 1

A water-soluble unsaturated monomer (1) was prepared by dissolving 1.8 g (0.05 mol % based on monomer) of N,N'-methylene bis-acrylamide as an internal cross-linking agent in 5,500 g of an aqueous solution containing partially neutralized (ratio of neutralization 75 mol %) sodium acrylate in a concentration of 37% by weight. This monomer (1) was placed in a-reaction vessel comprising a jacketed stainless steel twin-arm kneader of an inner volume of 10 liters provided with two sigma vanes and a lid fitted to the kneader, with the entrapped air displaced with nitrogen. Then, the monomer was stirred with the blade of the kneader and 0.3 mol % of ammonium persulfate and 0.03 mol % of sodium hydrogen sulfite were added meanwhile to the stirred monomer. The monomer began to polymerize one minute after the start of the stirring. A hydrogel polymer consequently formed was finely pulverized into particles about 5 mm in diameter 16 minutes after the start of the stirring. The hydrogel polymer thus produced was removed from the reaction vessel 60 minutes after the start of the polymerization and dried with hot air at 130° C. for 90 minutes. Irregular particles of absorbent resin (1) having 94% of a solid content were obtained by pulverizing the dry polymer with a shaking mill and separating a JIS 20-mesh pass portion of the resultant powder.

Production Example 2

A water-soluble unsaturated monomer (2) was prepared by following the procedure of Production Example 1 while using 1.36 g (0.02 mol % based on monomer) of trimethylol propane triacrylate in the place of N,N'-methylene bis-acrylamide. Then, the water-soluble unsaturated monomer (2) was polymerized in the same manner as in Production Example 1. Irregular particles of absorbent resin (2) having 97% of a solid content were obtained by drying the resultant gel polymer at 180° C. in the same manner as in Production Example 1.

Production Example 3

Into 500 ml of a four necked round flask provided a stirrer, a reflex condenser, a funnel and a nitrogen introducing tube, 230 ml of cyclohexane and 1.86 g of ethyl cellulose (N-200) as a dispersant were charged and heated to a temperature of 75° C. Further, 82 g of an aqueous solution containing partially neutralized (ratio of neutralization 80 mol %) sodium acrylate in a concentration of 45% by weight, 0.02 g of polyethylene glycol diacrylate (average n=8) (0.01 mol % based on monomer) and 0.1 g of potassium persulfate was charged to the funnel. Then the aqueous solution was dropped from the funnel into the four necked flask for 1.5 hours under nitrogen atmosphere, and further polymerization was carried out under maintaining dispersed solution of cyclohexane at a temperature of 70° to 75° C. for 30 minutes. After polymerization, a hydrated gel polymer in cyclohexane was subjected to reflex and azeotropic hydration with cyclohexame to obtain a hydrated spherical absorbent resin (3) having 65% by weight of a solid content.

EXAMPLE 1

An absorbent resin (a) having an average particle diameter of 350 μm was obtained by mixing 100 parts of the powdery absorbent resin (1) obtained in Production Example 1 with 3 parts of glycerin triacetate (boiling point 260° C.), 2 parts of water, and 8 parts of isopropanol and heating the resultant mixture at 210° C. for 2 hours. The results of the working examples and those of the controls cited herein are collectively shown in Table 1.

EXAMPLE 2

An absorbent resin (b) having an average particle diameter of 360 μm was obtained by following the procedure of Example 1 while changing the amount of water added to 6 parts and the duration of heating to 1 hour.

EXAMPLE 3

An absorbent resin (c) having an average particle diameter of 340 μm was obtained by mixing 100 parts of the powdery absorbent resin (1) with 3 parts of glycerol tripropionate, 2 parts of water, and 4 parts of ethanol and then heating the resultant mixture at 220° C. for 2 hours.

EXAMPLE 4

An absorbent resin (d) having an average particle diameter of 330 μm was obtained by mixing 100 parts of the powdery absorbent resin (2) obtained in Production Example 1 with 3.5 parts of glycerin tributyrate (boiling point 305° to 310° C.), 2 parts of water, and 10 parts of methanol and then heating the resultant mixture at 200° C. for 6 hours.

EXAMPLE 5

An absorbent resin (e) having an average particle diameter of 330 μm was obtained by mixing 100 parts of the powdery absorbent resin (1) with 10 parts of ethylene glycol diacetate (boiling point 191° C.), 2 parts of water, and 10 parts of methanol and then heating the resultant mixture at 190° C. for 4 hours.

EXAMPLE 6

An absorbent resin (f) having an average particle diameter of 330 μm was obtained by mixing 100 parts of the powdery absorbent resin (1) with 4 parts of propylene glycol diacetate, 2 parts of water, and 10 parts of methanol and then heating the resultant mixture at 230° C. for 30 minutes.

EXAMPLE 7

An absorbent resin (g) having an average particle diameter of 340 μm was obtained by mixing 100 parts of the powdery absorbent resin (1) with 20 parts of water and 80 parts of methanol and then 5 parts of glycerol diacetate (boiling point 182° C.), heating the resultant dispersed solution at 180° C. for 2 hours to evaporate and dry.

EXAMPLE 8

An absorbent resin (h) having 95% of a solid content and an average particle diameter of 200 μm was obtained by mixing 155 parts of the hydrated absorbent resin (3) with 5 parts of glycerol triacetate and dried and heat-treated at a temperature of 200° C. for 1 hour at the same time.

Control 1

The powdery absorbent resin (1) obtained in Production Example 1 was used in its unmodified form as an absorbent resin (a) for comparison.

Control 2

The powdery absorbent resin (2) obtained in Production Example 2 was used in its unmodified form as an absorbent resin (b) for comparison.

Control 3

An absorbent resin (c) for comparison was obtained by following the procedure of Example 1 while omitting the heat treatment subsequently to the addition of glycerol triacetate to the powdery absorbent resin (1).

Control 4

An absorbent resin (d) for comparison was obtained by following the procedure of Example 1 while changing glycerol triacetate to glycerol.

Control 5

An absorbent resin (e) for comparison was obtained by following the procedure of Example 2 while changing glycerol triacetate to glycerol triglycidyl ether.

Control 6

An absorbent resin (f) for comparison was obtained by following the procedure of Example 5 while changing ethylene glycol diacetate to ethylene glycol.

Control 7

An absorbent resin (g) for comparison was obtained by following the procedure of Example 6 while changing propylene glycol diacetate to ethylene glycol diglycidyl ether.

Control 8

An absorbent resin (h) for comparison having a solid content of 95% was obtained by adding 5 parts of glycerol into 155 parts of the hydrated absorbent resin (3) having a solid content of 65% by weight instead of glycerol triacetate by following the procedure of Example 8 and then drying and heat treating at the same time.

Control 9

The absorbent resin (3) obtained in Production Example 3 was used as an absorbent resin (i) for comparison as it is.

TABLE 1

|  | Obtained absorbent resin | (Powdery) absorbent resin used | Absorption capacity (without load) (g/g) | Absorption capacity under load (g/g) | suction power (g/g) | Hygroscopic flowability |
|---|---|---|---|---|---|---|
| Example 1 | (a) | (1) | 46 | 27 | 17.3 | ⊙ |
| Example 2 | (b) | (1) | 49 | 25 | 16.7 | ○ |
| Example 3 | (c) | (1) | 46 | 26 | 16.0 | ⊙ |
| Example 4 | (d) | (2) | 50 | 26 | 16.6 | ⊙ |
| Example 5 | (e) | (1) | 47 | 26 | 16.4 | ⊙ |
| Example 6 | (f) | (1) | 49 | 25 | 17.4 | ○ |
| Example 7 | (g) | (1) | 48 | 26 | 17.0 | ⊙ |
| Example 8 | (h) | (3) | 41 | 22 | 15.6 | ⊙ |
| Control 1 | (a) for comparison | (1) | 51 | 14 | 12.3 | Δ |

TABLE 1-continued

|  | Obtained absorbent resin | (Powdery) absorbent resin used | Absorption capacity (without load) (g/g) | Absorption capacity under load (g/g) | suction power (g/g) | Hygroscopic flowability |
|---|---|---|---|---|---|---|
| Control 2 | (b) for comparison | (2) | 64 | 11 | 9.6 | Δ |
| Control 3 | (c) for comparison | (1) | 48 | 13 | 11.6 | Δ |
| Control 4 | (d) for comparison | (1) | 42 | 27 | 16.9 | X |
| Control 5 | (e) for comparison | (1) | 44 | 24 | 16.2 | X |
| Control 6 | (f) for comparison | (1) | 43 | 26 | 16.3 | X |
| Control 7 | (g) for comparison | (1) | 46 | 24 | 16.4 | X |
| Control 8 | (h) for comparison | (3) | 26 | 8 | 7.9 | X |
| Control 9 | (i) for comparison | (3) | 29 | 9 | 4.6 | Δ |

What is claimed is:

1. A method for the surface treatment of an absorbent resin, comprising adding an organic carboxylic ester of a polyhydric alcohol having 0 or 1 hydroxyl group in the molecular unit thereof derived from a polyhydric alcohol to said absorbent resin and then heat-treating the resultant mixture.

2. A method according to claim 1, wherein said organic carboxylic ester of a polyhydric alcohol has no hydroxyl group.

3. A method according to claim 1, wherein said heat treatment is carried out at a temperature in the range of 100° to 300° C.

4. A method according to claim 1, wherein the amount of said organic carboxylic ester of a polyhydric alcohol is in the range of 0.01 to 20 parts by weight, based on 100 parts by weight of the solids of said absorbent resin.

5. A method according to claim 1, wherein said absorbent resin is in the form of a powder having an average particle diameter in the range of 100 to 1,000 μm.

6. A method according to claim 3, wherein said mixture coexists with water prior to said heat treatment.

7. A method according to claim 3, wherein said absorbent resin has a solids content of not less than 60% by weight.

8. A method according to claim 1, wherein said organic carboxylic ester of a polyhydric alcohol is directly mixed with said absorbent resin.

9. A method according to claim 1, wherein said organic carboxylic ester of a polyhydric alcohol is directly mixed with said absorbent resin together with an organic solvent.

10. A method according to claim 1, wherein said organic carboxylic ester of a polyhydric alcohol is directly mixed with said absorbent resin together with an organic solvent and water.

11. A method according to claim 1, wherein said organic carboxylic ester of a polyhydric alcohol is at least one member selected from the group consisting of formic esters, acetic esters, propionic esters, lactic esters, succinic half esters, fumaric half esters, tartaric half esters, and malic half esters of a polyhydric alcohol.

12. A method according to claim 11, wherein said polyhydric alcohol is at least one member selected from the group consisting of ethylene glycol, diethylene glycol, triethylene glycol, polyethylene glycol, diethanolamine, triethanolamine, glycerol, trimethylolpropane, 1,3-propanediol, 2,3-propanediol, pentaerythritol, sorbitol, and polyglycerol.

13. A method according to claim 1, wherein said organic carboxylic ester of a polyhydric alcohol is mixed with said absorbent resin dispersed in an inert solvent.

14. A method according to claim 1, wherein said organic carboxylic ester is produced from a lower carboxylic acid having less than 7 carbon atoms.

* * * * *